US006974793B2

(12) United States Patent
Donovan

(10) Patent No.: US 6,974,793 B2
(45) Date of Patent: *Dec. 13, 2005

(54) METHOD FOR TREATING PRIMARY HYPERPARATHYROID DISORDERS

(75) Inventor: Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 470 days.

This patent is subject to a terminal disclaimer.

(21) Appl. No.: 09/971,869

(22) Filed: Oct. 4, 2001

(65) Prior Publication Data

US 2002/0018786 A1 Feb. 14, 2002

Related U.S. Application Data

(60) Continuation of application No. 09/704,440, filed on Nov. 1, 2000, now Pat. No. 6,328,977, which is a division of application No. 09/510,711, filed on Feb. 22, 2000, now abandoned.

(51) Int. Cl.[7] .......................... G01N 33/78; G01N 33/74
(52) U.S. Cl. ........................................... 514/2; 436/500
(58) Field of Search .............................. 514/2; 436/500

(56) References Cited

U.S. PATENT DOCUMENTS

| 5,667,808 A | 9/1997 | Johnson et al. |
| 5,674,205 A | 10/1997 | Pasricha et al. |
| 5,766,605 A | 6/1998 | Sanders et al. |

(Continued)

FOREIGN PATENT DOCUMENTS

| WO | WO94/21300 | 9/1994 |

OTHER PUBLICATIONS

Ahren, B.; *Cholinergic and VIPergic Effects on Thyroid Hormone Secretion in the Mouse*; Peptides; 6:585–589 (1985).
Amenta, F., et al.; *Cholinergic Nerves in the Thyroid Gland*; Cell and Tissue Res.; 195:367–370 (1978).
Aoki, K.R.; *Preclinical Update on BOTOX®(botulinum Toxin Type A)–Purified Neurotoxin Complex Relative to other Botulinum Neurotoxin Preparations*;Eur. J. Neurol; 6(Suppl 4):S3–S10; (1999).
Boyd, R.S., et al.; *The Effect of Botulinum Neurotoxin–B on Insulin Release from a B–Cell Line*; Movement Disorders; vol. 10, No. 3; Item 19; 376 (1995).
Boyd, R.S., et al.; *The Insulin Secreting B–Cell Line HIT–15 Contains SNAP–25 Which is a Target for Botulinum Neurotoxin–A*; Movement Disorders; vol. 10, No. 3; Item 20; 376 (1995).
Brandi, M.L., et al.; *Interaction of VIPergic and Cholinergic Receptors in Human Thyroid Cell*; Peptides; 8:893–897 (1987).
Braverman, L.E. (Editor); *Diseases of the Thyroid*; Humana Press; p. 157 (1997).
Cardinali, D.P., et al.; *Peripheral Neuroendocrinology of the Cervical Autonomic Nervous System*; Brazilian J. Med. Biol. Res.; 27(3):573–599 (1994).
Fauci, A.S., et al. (Editors); *Harrison's Principles of Internal Medicine*, 14th Edition; McGraw–Hill (1998).
Garry, M.G., et al.; *Evaluation of the Efficacy of a Bioerodible Bupivacaine Polymer System on Antinociception and Inflammatory Mediator Release*; Pain; 82(1);49–55 (1999).
Gonelle–Gispert, C., et al.; *SNAP–25A AND–25B Isoforms are Both Expressed in Insulin–Secreting Cells and Can Function in Insulin Secretion*; Biochem. J.; 339:159–165 (1999).
Huffman, L.J., et al.; *Muscarinic Modulation of the Vasodilatory Effects of Vasodilatory Effects of Vasoactive Intestinal Peptide at the Rat Thyroid Gland*; Neuroendocrinology; 53:69–74 (1991).
Lakomy, M., et al.; *Acetylcholine Esterase Positive Nerves in Swine Thyroid*; Z. mikrosk.–anat. Forsch., Leipzig 100, 1, S. 34–38 (1986).
Laskawi, R., et al.; *Up–to–Date Report of Botulinum Toxin Type A Treatment in Patients with Gustatory Sweating (Frey's Syndrome)*; Laryngoscope 108; 381–384 (Mar. 1998).
Longley, R.S., et al.; *Effect of the Parasympathetic System on Calcitonin Secretion*; Clin Res; 27:657A (1979).
Lopez–Muniz, A., et al.; *Etude des terminaisons nerveuses au contact des cellules parafolliculaires de la thyroide*; Annales d'Endocrinologie (Paris); 59:3–8 (1998).
Melander, A., et al.; *Presence and Influence of Cholinergic Nerves in the Mouse Thyroid*; Endocrinology; 105(1):7–9 (1979).
Mercadante, S., et al.; *Celiac Plexus Block: A Reappraisal*; Regional Anesthesia and Pain Medicine; 23(1):37–48 (Jan.–Feb. 1998).
Powell, E.M., et al.; *Controlled Release of Nerve Growth Factor from a Polymeric Implant*; Brain Res; 515(1–2):309–311 (1990).
Rao, J.K., et al.; *Implantable Controlled Delivery Systems for Proteins Based on Collagen—pHEMA Hydrogels*; Biomaterials; 15(5):383–389 (1994).

(Continued)

Primary Examiner—Jon Weber
Assistant Examiner—Samuel Wei Liu
(74) Attorney, Agent, or Firm—Stephen Donovan; Martin A. Voet; Robert J. Baran

(57) ABSTRACT

A method for treating hypoparathyroidism and/or hypocalcemia by local administration of a neurotoxin, such as a botulinum toxin, to a parathyroid gland, thereby reducing an inhibitory effect upon parathyroid hormone secretion. A method for treating hyperparathyroidism and/or hypercalcemia by local administration of a neurotoxin, such as a botulinum toxin, to a sympathetic ganglion which innervates a parathyroid hormone secreting parathyroid cell, thereby reducing a stimulatory effect upon parathyroid hormone secretion.

12 Claims, No Drawings

U.S. PATENT DOCUMENTS 5,980,945 A 11/1999 Ruiz
6,007,843 A 12/1999 Drizen et al.
6,011,011 A 1/2000 Hageman
6,022,554 A 2/2000 Lee et al.

OTHER PUBLICATIONS

Ragona, R.M., et al.; *Management of Parotid Sialocete with Botulinum Toxin;* Laryngoscope 109; 1344–1346 (Aug. 1999).

Schantz, E.J. et al.; *Properties and Use of Botulinum Toxin and Other Microbial Neurotoxins in Medicine;* Microbiological Reviews; vol. 56, No. 1; 80–99 (Mar. 1992).

Singh, B.R.; *Critical Aspects of Bacterial Protein Toxins; Natural Toxins II;* Plenum Press, New York; pp. 63–84 (1996).

Stern, J.E., et al.; *Influence of the Autonomic Nervous System on Calcium Homeostasis in the Rat;* Biol Signals; 3:15–25 (1994).

Stern, J.E., et al.; *Parasympathetic Control of Parathyroid Hormone and Calcitonin Secretion in Rats;* Journal of the Autonomic Nervous System; 48:45–53 (1994).

Stevens, P.D., et al.; *Managing Chronic Pancreatitis Pain: A Block in Time;* AJG; 94(4):872–874 (1999).

Unger, J., et al.; *Mechanism of Cholinergic Inhibition of Dog Thyroid Secretion In Vitro;* Endocrinology; 114:1266–1271 (1984).

Williams, G.A., et al.; *Effect of the Parasympathetic System on Secretion of Parathyroid Hormone;* Metabolism; vol. 34, No. 7; 612–615 (Jul. 1985).

METHOD FOR TREATING PRIMARY HYPERPARATHYROID DISORDERS

CROSS REFERENCE

This application is a continuation of application Ser. No. 09/704,440, filed Nov. 1, 2000, now U.S. Pat. 6,328,977, issued Dec. 11, 2001, which is a divisional of application Ser. No. 09/510,711, filed Feb. 22, 2000, now abandoned.

BACKGROUND

The present invention relates to methods for treating parathyroid disorders. In particular the present invention relates to methods for treating parathyroid disorders by administration of a neurotoxin to a patient.

The adult human typically has four small parathyroid glands, each weighing about 30 to 40 mg, located near the thyroid. The chief cells of the parathyroid glands can make and release parathyroid hormone (PTH), which functions to help maintain serum calcium homeostasis. Parathyroid hormone increases blood calcium level while calcitonin from the thyroid C cells acts to lower it.

Disorders of the parathyroid glands include hyperparathyroidism and hypoparathyroidism. Primary hyperparathyroidism is about twice as prevalent in females as it is in males, and this ratio increases with age. About 1 in 500 females over age of 40 and 1 in 2000 males over the age of 40 has primary hyperparathyroidism. In the United States about 250,000 persons are afflicted with primary hyperparathyroidism.

Primary hyperparathyroidism exists when a disorder of parathyroid tissue itself, as the primary defect, results in the release into the circulation of too much parathyroid hormone. Among the known causes of primary hyperparathyroidism are parathyroid adenoma, hyperplasia and carcinoma. Secondary hyperparathyroidism is a reactive parathyroid hyperplasic phenomenon, which can accompany renal failure. Symptoms of hyperparathyroidism can include nephrolithiasis, bone disease, peptic ulcer, fatigue and hypertension.

Untreated hyperparathyroidism can result in the loss of considerable amounts of bone mass due to the hypercalcemia which arises from an excessive level of circulating parathyroid hormone. Thus a high level of parathyroid hormone causes osteoclastic bone reabsorption which can lead to multiple foci of bone destruction, osteitis fibrosa cystica or von Recklinghausen's disease of bone.

Production of parathyroid hormone by the chief cells of the parathyroid glands is apparently regulated to a significant extent in the normal parathyroid by both free calcium concentration in extracellular fluid and by levels of 1,25 dihydroxyvitamin D (calcitriol). Parathyroid hormone is a single chain, 84 amino acid residue polypeptide which acts upon osteocytes and osteoclasts to increase the rate of release of calcium from blood into bone, apparently by stimulation of osteocytic osteolysis.

The treatment of choice for primary hyperparathyroidism is surgery to remove all or most of the hyperactive parathyroid tissue. Thallium-technetium subtraction scans, ultrasound, selective venous sampling, computed tomography (CT), magnetic resonance imaging (MRI), and arteriography have been used to localize a parathyroid disorder. Unfortunately, it has been reported that in about one third of parathyroidectomies, surgery fails to cure the hyperparathyroidism because of surgical ineptness to remove the appropriate tissues. Furthermore, excessive removal of parathyroid glands tissue can cause tetany. Complications of parathyroidectomy can include hematoma, vocal cord paralysis, hypocalcemia, and persistent hypercalcemia. Thus, after parathyroidectomy 5% of patients have permanent hypocalcemia, which therefore requires daily oral supplementation or reimplantatiori of cryopreserved parathyroid tissue.

Significantly, while parathyroid adenoma can be treated by removal of the one abnormal parathyroid gland, removal of multiple parathyroid glands is typically required to treat parathyroid hyperplasia. Furthermore, the cause or causes of primary parathyroid hyperplasia are unknown.

Alternates to surgery for primary hyperparathyroidism include ethanol block and embolization. Block by ethanol injection destroys the parathyroid gland or glands injected and can cause Homer's syndrome and vocal cord paralysis. Additionally, embolization to the artery supplying an abnormal parathyroid gland while sometimes successful to infarct the parathyroid gland and normalize calcium levels, is a difficult procedure with a limited success rate.

Primary hypoparathyroidism due to deficient PTH secretion can cause a low serum calcium due to a lack of PTH mediated bone resorption and calcium reabsorption by the kidneys. Symptoms of hypocalcemia include neuromuscular irritability and tetany. Intravenous calcium is the treatment of choice for primary hypoparathyroidism. Notably, PTH replacement has also been used to treat primary hypoparathyroidism. Drawbacks to PTH replacement include lack of clinical experience, it must be given by injection and it is expensive.

Parathyroid Innervation

With regard to parathyroid innervation, one view is that the nerves to the parathyroids are only vasomotor, not secretomotor in nature, and that parathyroid activity is controlled solely by variation in blood calcium level. Thus, a rise in blood calcium level inhibits PTH release, while a fall in blood calcium level stimulates PTH release.

Significantly it has been reported that parasympathetic influences inhibit parathyroid hormone secretion, that cholinergic agonists decrease serum PTH and that this effect is blocked by atropine. See e.g. *J. Auto Nerv Syst* 1994;48:45–53, *Metabolism* 1985;34(7):612–615 and *Brazilian J Med Biol Res* 1994;27:573–599.

Additionally, the close anatomic association of the thyroid and parathyroid glands makes it reasonable to assume that the parathyroids are innervated in a manner similar to the thyroid. The two upper parathyroid glands are located adjacent to the posterior surface of the upper or, middle part of the thyroid lobe, often just anterior to the recurrent laryngeal nerve as it enters the larynx. The two lower parathyroid glands are usually found on the lateral or posterior surfaces of the lower part of the thyroid gland or within several centimeters of the lower thyroid pole within the thymic tongue.

It is known that the thyroid gland receives innervation from both the sympathetic and parasympathetic divisions of the autonomic nervous system. The sympathetic fibers arise from the cervical ganglia and enter with blood vessels, whereas the parasympathetic fibers are derived from the vagus and reach the gland via branches of the laryngeal nerves. The thyroid gland's relation to the recurrent laryngeal nerves and to the external branch of the superior laryngeal nerves is of major surgical significance, since damage to these nerves can lead to a disability of phonation.

Sympathetic innervation of the thyroid cells has been reported to exert a stimulatory effect upon thyroid hormone release through adrenergic receptors for norepinephrine on follicle cells. *Endocrinology* 1979;105:7–9. Significantly, the human thyroid is also innervated by cholinergic, parasympathetic fibers. *Cell Tiss Res* 1978;195:367–370. See also *Biol Signals* 1994;3:15–25. And other mammalian species are known to also have cholinergicly innervated thyroid cells. See e.g. *Z. Mikrosk Anat Forsch Leipzig* 1986;100:1,S, 34–38 (pig thyroid is cholinergicly innervated); *Neuroendocrinology* 1991;53:69–74 (rat thyroid is cholinergicly innervated); *Endocrinology* 1984;114:1266–1271 (dog thyroid is cholinergicly innervated);

Significantly, the consensus is that cholinergic, parasympathetic influence upon thyroid hormone secretion by thyroid follicle cells in inhibitory. *Endocrinology* 1979;105:7–9; *Endocrinology* 1984;114:1266–1271; *Peptides* 1985;6:585–589; *Peptides* 1987;8:893–897, and; *Brazilian J Med Biol Res* 1994;27:573–599. The direct cholinergic influence upon the thyroid appears to be mediated by muscarinic acetylcholine receptors of thyroid follicle cells since the cholinergic inhibition is blocked by atropine. *Endocrinology* 1979;105:7.

Thus, one can conclude that, at least in some circumstances, the deficient PTH secretion of primary hypoparathyroidism is influenced by inhibitory parasympathetic innervation of the parathyroids, while primary parathyroid hyperplasia is influenced by excessive sympathetic stimulation of the parathyroids.

Botulinum Toxin

The anaerobic, gram positive bacterium *Clostridium botulinum* produces a potent polypeptide neurotoxin, botulinum toxin, which causes a neuroparalytic illness in humans and animals referred to as botulism. The spores of Clostridium botulinum are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

[1]Available from Allergan, Inc., of Irvine, Calif. under the tradename BOTOX® in 100 unit vials. One unit of BOTOX® contains about 50 picograms of botulinum toxin type A complex.

Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Significantly, it is known that the cytosol of pancreatic islet B cells contains at least SNAP-25 (*Biochem J* 1;339 (pt 1): 159–65 (April 1999)), and synaptobrevin (*Mov Disord* 1995 May; 10(3): 376).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 500 RD complex. Botulinum toxin type D is produced as both 300 RD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephnne from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, calcitonin gene-related peptide (CGRP) and glutamate.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56:80–99 (1992). Generally, the botulinum toxin type A complex can be isolated and purified from an anaerobic fermentation by cultivating Clostridium botulinum type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2\times 10^8$ $LD_{50}$ U/mg or greater; purified botulinum toxin type B with an approximately 156 kD molecular weight with a specific potency of $1-2\times 10^8$ $LD_{50}$ U/mg or greater, and; purified botulinum toxin type F with an approximately 155 kD molecular weight with a specific potency of $1-2\times 10^7$ $LD_{50}$ U/mg or greater.

Already prepared and purified botulinum toxins and toxin complexes suitable for preparing pharmaceutical formulations can be obtained from List Biological Laboratories, Inc., Campbell, Calif.; the Centre for Applied Microbiology and Research, Porton Down, U.K.; Wako (Osaka, Japan), as well as from Sigma Chemicals of St Louis, Mo.

Pure botulinum toxin is so labile that it is generally not used to prepare a pharmaceutical composition. Furthermore. the botulinum toxin complexes, such a the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin must be stabilized with a stabilizing agent. The only successful stabilizing agent for this purpose has been the animal derived proteins albumin and gelatin. And as indicated, the presence of animal derived proteins in the final formulation presents potential problems in that certain stable viruses, prions or other infectious or pathogenic compounds carried through from donors can contaminate the toxin.

Furthermore, any one of the harsh pH, temperature and concentration range conditions required to lyophilize (freeze-dry) or vacuum dry a botulinum toxin containing pharmaceutical composition into a toxin shipping and storage format (ready for use or reconstitution by a physician) can detoxify the toxin. Thus, animal derived or donor pool proteins such as gelatin and serum albumin have been used with some success to stabilize botulinum toxin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of Clostridium botulinum grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin and 0.9 milligrams of sodium chloride in a sterile, vacuum-dried form without a preservative.

To reconstitute vacuum-dried BOTOX® sterile normal saline without a preservative; 0.9% Sodium Chloride Injection is used by drawing up the proper amount of diluent in the appropriate size syringe. Since BOTOX® is denatured by bubbling or similar violent agitation, the diluent is gently injected into the vial. BOTOX® should be administered within four hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer at or below −5° C. BOTOX® is administered within four hours after the vial is removed from the freezer and reconstituted. During these four hours, reconstituted BOTOX® can be stored in a refrigerator (2° to 8° C.). Reconstituted BOTOX® is clear, colorless and free of particulate matter.

It has been reported that botulinum toxin type A has been used in clinical settings as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimus: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX). Peak muscle weakness and duration were dose related for all serotypes. DAS $ED_{50}$ values (units/kg) were as follows: BOTOX®: 6.7, Dysport®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, Dysport®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of botulinum toxin type B. *Eur J Neurol* 1999 Nov;6(Suppl 4):S3–S10.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

What is needed therefore is an effective, long lasting, non-surgical resection, non-radiotherapy, non-systemic drug administration, therapeutic drug and method for treating parathyroid disorders.

SUMMARY

The present invention meets this need and provides an effective, non-surgical resection, long term, non-radiotherapy, non-systemic drug administration, therapeutic method for treating parathyroid disorders.

The drug within the scope of this invention for treating parathyroid disorders is a neurotoxin. Significantly, the same neurotoxin can be used to treat hyperparathyroidism, hypoparathyroidism, hypocalcemia and hypercalcemia depending upon factors such as the site of local administration of the neurotoxin and the amount of neurotoxin to be administered.

As used herein "local administration" means direct injection of a neurotoxin into a parathyroid gland or into a sympathetic ganglion which innervates a parathyroid PTH secretory cell. Systemic routes of administration, such as oral and intravenous routes of administration, are excluded from the scope of "local administration" of a neurotoxin.

A method for treating a parathyroid disorder according to the present invention can be carried out by administration of a therapeutically effective amount of a neurotoxin to a patient, thereby treating the parathyroid disorder. The neurotoxin can administered to a parathyroid gland of the patient when the parathyroid disorder to be treated is hypoparathyroidism. Alternately, the neurotoxin can be administered to a sympathetic ganglion which innervates a parathyroid PTH secreting cell when the parathyroid disorder to be treated is hyperparathyroidism.

A detailed method for treating a parathyroid disorder according to the present invention can comprise the step of administration of a therapeutically effective amount of a botulinum toxin to a patient. Thus, a method for treating hypoparathyroidism according to the present invention can comprise the step of local administration to a parathyroid gland (i.e. to one or more of the four normally present parathyroid glands) of a therapeutically effective amount of a botulinum toxin, thereby increasing a deficient parathyroid hormone secretion from a parathyroid cell which is capable of secreting parathyroid hormone, and effectively treating the hypoparathyroidism. Furthermore, a method within the scope of the present invention for treating hyperparathyroidism, can comprise the step of local administration to a sympathetic ganglion which innervates a parathyroid PTH secreting cell of a parathyroid gland of a therapeutically effective amount of a botulinum toxin, thereby reducing an excessive parathyroid hormone secretion from the parathyroid cell and hence effectively treating the hyperparathyroidism.

The neurotoxin can be administered in an amount of between about $10^{-3}$ U/kg and about 35 U/kg. 35 U/kg is an upper limit because it approaches a lethal dose of certain neurotoxins, such as botulinum toxin type A. Other botulinum toxins, such as botulinum toxin type B, can be safely administered at several orders of magnitude higher dosage. Preferably, the neurotoxin is administered in an amount of between about $10^{-2}$ U/kg and about 25 U/kg. More preferably, the neurotoxin is administered in an amount of between about $10^{-1}$ U/kg and about 15 U/kg. Most preferably, the neurotoxin is administered in an amount of between about 1 U/kg and about 10 U/kg. In many instances, an administration of from about 0.1 units to about 300 units of a neurotoxin, such as a botulinum toxin type A, provides effective and long lasting therapeutic relief. More preferably, from about 0.1 unit to about 100 units of a neurotoxin, such as a botulinum toxin type A, can be used and most preferably, from about 0.1 unit to about 50 units of a neurotoxin, such as a botulinum toxin type A, can be locally administered into a target tissue such as the thyroid or a sympathetic ganglion with efficacious results. In a particularly preferred embodiment of the present invention, a parathyroid gland or a sympathetic ganglion which innervates a parathyroid gland, can be locally administered with from about 1 unit to about 20 units of a neurotoxin (such as botulinum toxin type A) to achieve therapeutically effective results.

The neurotoxin can be made by a Clostridial bacterium, such as by a *Clostridium botulinum, Clostridium butyricum, Clostridium beratti* or *Clostridium tetani* bacterium. Additionally, the neurotoxin can be a modified neurotoxin, that is a neurotoxin that has at least one of its amino acids deleted, modified or replaced, as compared to the native or wild type neurotoxin. Furthermore, the neurotoxin can be a recombinant produced neurotoxin or a derivative or fragment thereof.

The neurotoxin can be a botulinum toxin, such as one of the botulinum toxin serotypes A, B, $C_1$, D, E, F or G. Preferably, the neurotoxin is botulinum toxin type A and the neurotoxin is locally administered by direct injection of the neurotoxin into a parathyroid gland or into a sympathetic ganglion which innervates the parathyroid gland.

A detailed embodiment of a method within the scope of the present invention for treating a parathyroid disorder can comprise the step of injecting a therapeutically effective amount of a botulinum toxin into a parathyroid gland of a human patient, thereby increasing a parathyroid hormone (PTH) secretion from a parathyroid hormone secreting parathyroid cell of the parathyroid gland and treating a parathyroid disorder.

Another detailed embodiment of a method within the scope of the present invention for treating a parathyroid disorder of a human patient can comprise the step of local administration to a cholinergic influenced parathyroid PTH secreting cell of a parathyroid gland of a human patient of a therapeutically effective amount of botulinum toxin type A, thereby increasing a cholinergic influenced deficient parathyroid hormone secretion from the parathyroid cell of the parathyroid gland and treating the parathyroid disorder.

Another method within the scope of the present invention is a method for treating a parathyroid disorder by administration of a neurotoxin to a sympathetic nervous system of a patient. In this method the neurotoxin is locally administered to a sympathetic ganglion which innervates a parathyroid hormone secreting parathyroid cell and the parathyroid disorder is hyperparathyroidism.

A detailed embodiment of a method within the scope of the present invention for treating a parathyroid disorder of a human patient can comprise the step of in vivo, local administration to a sympathetic ganglion, which innervates a parathyroid hormone secreting prothyroid cell of a parathyroid gland of a patient, of a therapeutically effective amount of a botulinum toxin, thereby decreasing an excessive parathyroid hormone secretion from the parathyroid cell of the parathyroid gland and treating hyperparathyroidism.

A detailed embodiment of the present invention is a method for treating a parathyroid disorder by injecting a therapeutically effective amount of a botulinum toxin into a parathyroid gland of a human patient, thereby increasing a secretion of a parathyroid hormone from a parathyroid cell and treating the parathyroid disorder. Preferably, the secretion treated is a cholinergic influenced secretion and the botulinum toxin used is botulinum toxin type A, although the botulinum toxin can selected from the group consisting of botulinum toxin types A, B, C (i.e. $C_1$), D, E, F and G.

My invention also includes within its scope, a method for treating hypocalcemia, the method comprising the step of local administration to a parathyroid hormone secreting parathyroid cell of a parathyroid gland of a therapeutically effective amount of a botulinum toxin, thereby increasing a deficient parathyroid hormone secretion from the parathyroid cell and treating hypocalcemia. Additionally, my invention also includes within its scope a method for treating hypercalcemia, the method comprising the step of local administration to a sympathetic ganglion which innervates a parathyroid hormone secreting parathyroid cell of a parathyroid gland of a therapeutically effective amount of a botulinum toxin, thereby decreasing an excessive parathyroid hormone secretion from the parathyroid cell of the parathyroid gland and treating hypercalcemia.

DESCRIPTION

The present invention is based upon the discovery that a parathyroid disorder can be treated by in vivo administration of a neurotoxin to a patient. Thus administration of a neurotoxin to a parathyroid gland of a patient can remove an inhibitory cholinergic effect upon parathyroid hormone secretion by the parathyroid gland, thereby providing an effective treatment for hypoparathyroidism and/or hypocalcemia. Additionally, administration of a neurotoxin to a sympathetic ganglion which innervates a parathyroid hormone secretory cell of a parathyroid gland can remove a stimulatory adrenergic effect upon parathyroid hormone secretion, thereby providing an effective treatment for hyperparathyroidism and/or hypercalcemia.

Thus, parathyroid disorders can be treated, according to the present invention, by the alternative therapies of (a) local administration of a neurotoxin to one or more of the parathyroid glands, or; (b) local administration of a neurotoxin to a parathyroid gland innervating sympathetic ganglion of a patient, thereby resulting in, respectively, an increase of a secretion from a parathyroid cell, or a decrease in a secretion from a parathyroid chief (PTH secretory capable) cell I have discovered that a particular neurotoxin, botulinum toxin, can be used with dramatic ameliorative effect to treat a parathyroid disorder, thereby significantly superseding thereby current therapeutic regimens, such as surgical removal of parathyroid gland tissue to treat hyperparathyroidism and calcium supplementation to treat hypoparathyroidism.

Significantly, a single local administration of a neurotoxin, such as a botulinum toxin to one or more of the parathyroid glands, according to the present invention, can increase parathyroid hormone secretion and thereby treat symptoms of hypoparathyroidism. I have also discovered that a single local administration of a neurotoxin, such as a botulinum toxin to one or more of the sympathetic ganglia which innervate a parathyroid gland, according to the present invention, can reduce parathyroid hormone secretion and thereby treat symptoms of hyperparathyroidism. In either case, the symptoms of the parathyroid disorder can be alleviated for at least about from 2 months to about 6 months per neurotoxin administration. Notably, it has been reported that glandular tissue treated by a botulinum toxin can show a reduced secretory activity for as long as 27 months post injection of the toxin. *Laryngoscope* 1999;109:1344–1346, *Laryngoscope* 1998;108:381–384. My invention also includes within its scope the use of an implanted sustained release neurotoxin complex so as to provide therapeutic relief from a chronic parathyroid disorder. Thus, the neurotoxin can be imbedded within, absorbed, or carried by a suitable polymer matrix which can be implanted or embedded in or on a parathyroid gland or is sympathetic ganglion so as to provide a year or more of delayed and controlled release of the neurotoxin to the desired target tissue.

The hypoparathyroidism treatable by the present invention is primary hypoparathyroidism. Secondary hypoparathyroidism is not treatable by the present invention, because the present invention is based upon a therapeutic, local administration of a neurotoxin to one or more of the parathyroid glands and/or to a sympathetic ganglion which innervates the one or more of the parathyroid glands. Additionally the primary hypoparathyroidism treatable by the present invention is hypoparathyroidism which has as a causative factor the inhibitory activity upon parathyroid hormone secretion of cholinergic, parasympathetic innervation of the parathyroid.

Similarly, the hyperparathyroidism treatable by the present invention is primary hyperparathyroidism. Secondary hyperparathyroidism is not treatable by the present invention, because the present invention is based upon a therapeutic, local administration of a neurotoxin to one or more of the parathyroid glands and/or to a sympathetic ganglion which innervates the one or more of the parathyroid glands. Additionally the primary hyperparathyroidism treatable by the present invention is hyperparathyroidism which has as a causative factor the stimulatory activity upon parathyroid hormone secretion of sympathetic innervation of the parathyroid.

Notably, hypoparathyroidism resulting from a combination of factors, including inhibitory parasympathetic activity, is treatable by a method within the scope of the present invention. Similarly, hyperparathyroidism resulting from a combination of factors, including stimulatory sympathetic activity, is treatable by a method within the scope of the present invention.

Local Administration of a Neurotoxin to the Parathyroid

A preferred embodiment of the present invention is to inject a parathyroid gland of a patient with from 0.1 to 100 units, more preferably from 1 to 50 units, and most preferably from 1 to 10 units of a neurotoxin (such as a botulinum toxin type A), to thereby cause an increase of parathyroid hormone secretion. The present invention also includes within its scope treatment of a parathyroid disorder due to hyperplasic, hypertonic or hypertrophic parathyroid chief cells. A parathyroid disorder can be effectively treated by local administration of a neurotoxin, such as for example 0.1 to 100 units of botulinum toxin type A, to cholinergic, postganglionic, parasympathetic neurons which innervate the dysfunctional, parathyroid cells. Without wishing to be bound by theory, the botulinum toxin is believed to act to increase parathyroid hormone secretion by inhibiting release of acetylcholine neurotransmitter from cholinergic, postganglionic parasympathetic fibers which provide inhibitory innervation of parathyroid PTH secreting cells.

A neurotoxin, such as a botulinum toxin, locally administered in vivo to the parathyroid to thereby remove an inhibitory effect upon a secretory activity of a parathyroid hormone secreting parathyroid cell. The parathyroid hormone secreting parathyroid cell is cholinergically innervated such that the proteolytic light chain of the toxin is internalized by a cholinergic neuron which inhibitoraly influences a secretory activity of the parathyroid hormone secreting parathyroid cell.

Thus, cholinergically innervated parathyroid cells can be treated by local administration of a neurotoxin, such as a botulinum toxin. By local administration, of a parathyroid gland, it is meant that the neurotoxin is administered directly to or to the immediate vicinity of the parathyroid tissue to be treated.

The specific dosage appropriate for administration is readily determined by one of ordinary skill in the art according to the factor discussed above. The dosage can also depend upon the size of the parathyroid tissue mass to be treated or denervated, and the commercial preparation of the toxin. Additionally, the estimates for appropriate dosages in humans can be extrapolated from determinations of the amounts of botulinum required for effective denervation of other tissues. Thus, the amount of botulinum A to be injected is proportional to the mass and level of activity of the thyroid tissue to be treated. Generally, between about 0.01 and 35 units per kg of patient weight of a botulinum toxin, such as botulinum toxin type A, can be administered to effectively accomplish a toxin induced parathyroid tissue secretion down regulation upon administration of the neurotoxin into the thyroid. Less than about 0.01 U/kg of a botulinum toxin does not have a significant therapeutic effect upon the secretory activity of a parathyroid cell, while more than about 35 U/kg of a botulinum toxin approaches a toxic dose the neurotoxin. Careful placement of the injection needle and a low volume of neurotoxin used prevents significant amounts of botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the thyroid tissue to be treated and the administration route chosen. Botulinum toxin type A is a preferred botulinum toxin serotype for use in the methods of the present invention.

Diagnostic aids to determine hyper or hypoparathyroidism, by localization of the dysfunctional parathyroid tissue, include thallium-201/technetium-99m subtraction scintigraphy, computed tomography, ultrasonography, and magnetic resonance. Localization studies help by suggesting the most direct approach to the abnormal parathyroid tissue including whether surgery begins with a neck or mediastinal exploration. Particular scintigraphic techniques used to localize hyper or hypoplasic parathyroid glands, have included a combination of radiotracers including thallium-201 chloride or technetium-99m sestamibi and technetium-99m-sodium pertechnetate or iodine-123 sodium iodide. The processing of digital images obtained includes background correction and subtraction of the parathyroid image from the composite parathyroid and parathyroid image. These methods exploit the different biological behavior and tissue distribution of the two tracers, namely the parathyroid specific pertechnetate or iodine uptake relative to the more diffuse perfusion dependent distribution of thallium or sestamibi.

It has been reported that the neuronal selectivity of clostridial neurotoxins is a result of a very selective binding and cell entry mechanism. Although a site of action of botulinum toxin is the neuromuscular junction, where the toxin binds rapidly and prevents the release of acetylcholine from cholinergic neurons, it is known that clostridial neurotoxins are able to enter certain neurosecretory cells (for example PC12 cells) via a low affinity receptor if high concentrations of the neurotoxin are incubated with the cells for prolonged periods. This process appears to use a pathway via a receptor which is distinct from the highly specific and high affinity receptor present at the neuromuscular junction. Additionally, it has been reported that certain clostridial toxins have effects on phagocyte cells, such as macrophages, where entry into the cell is presumed to be via the specific phagocytic activity of these cells. Furthermore, incubation of certain adipocytes (i.e. fat cells) with botulinum toxin type A has been reported to inhibit glucose uptake by the adipocytes. The mechanism of the glucose uptake inhibition is apparently due to toxin inhibition of plasma membrane fusion or docking of cytosolic, recyclable membrane vesicles (RMVs), the RMVs containing glucose transporter proteins. PCT publication WO 94/21300.

Thus, while it is known that the botulinum toxins have a known binding affinity for cholinergic, pre-synaptic, peripheral motor neurons, it has been reported that botulinum toxins can also bind to and translocate into a variety of non-neuronal secretory cells, where the toxin then acts, in the known manner, as an endoprotease upon its respective secretory vessel-membrane docking protein. Because of the relatively lower affinity of the botulinum toxins for secretory cells, such as parathyroid cells, as compared to the affinity of the botulinum toxin for the cholinergic neurons which innervate parathyroid chief cells, the botulinum toxin can be injected into secretory or glandular tissues to provide a high local concentration of the toxin, thereby facilitating effect of the toxin upon both cholinergic neuron and directly upon parathyroid secretory cell. Thus, the present invention is applicable to the treatment of parathyroid disorders in circumstances where the target parathyroid secretory cells have little or no cholinergic innervation. Local administration of a neurotoxin to the parathyroids at a high dose level is carried out to treat primary hyperparathyroidism.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known safe and efficacious use for the treatment of skeletal muscle and smooth muscle disorders when locally administered by intramuscular injection.

The present invention includes within its scope the use of any neurotoxin which has a long duration therapeutic effect when locally applied to treat a parathyroid cell disorder of a patient. For example, neurotoxins made by any of the species of the toxin producing *Clostridium* bacteria, such as *Clostridium botulinum, Clostridium butyricum*, and *Clostridium beratti* can be used or adapted for use in the methods of the present invention. Additionally, all of the botulinum serotypes A, B, C, D, E, F and G can be advantageously used in the practice of the present invention, although type A is the most preferred serotype, as explained above. Practice of the present invention can provide effective relief of a parathyroid disorder for from 2–27 months or longer in humans from a single injection of the neurotoxin.

Botulinum toxin is believed to be able to block the release of any vesicle mediated exocytosis from any secretory (i.e. neuronal, glandular, secretory, chromaffin) cell type, as long as the light chain of the botulinum toxin is translocated into the intracellular medium. For example, the intracellular protein SNAP-25 is widely distributed in both neuronal and non-neuronal secretory cells and botulinum toxin type A is an endopeptidase for which the specific substrate is SNAP-25. Thus, while cholinergic neurons have a high affinity acceptor for the botulinum and tetanus toxins (and are therefore more sensitive than other neurons and other cells to the inhibition of vesicle mediated exocytosis of secretory compounds), as the toxin concentration is raised, non-cholinergic sympathetic neurons, chromaffin cells and other cell types can take up a botulinum toxin and show reduced exocytosis.

Hence, by practice of the present disclosed invention secretory parathyroid cells with little or no cholinergic innervation can be treated by use of an appropriately higher concentration of a botulinum toxin to bring about therapeutic relief from a parathyroid disorder such as primary hyperparathyroidism. Local administration to a parathyroid gland of a lower dose neurotoxin (i.e. from about 1 unit to about 20 units of botulinum toxin type A per parathyroid gland) can be used to teat hypoparathyroidism, as previously set forth.

Local Administration of a Neurotoxin to a Sympathetic Ganglion

Significantly, a method within the scope of the present invention for reducing an excessive parathyroid hormone secretion from a parathyroid gland comprises the step of local administration of a neurotoxin to the sympathetic nervous system. Sympathetic innervation of the parathyroid is know to exist. Thus, sympathetic nerve fibers can inhibit parathyroid hormone secretion by acting via adrenergic receptors on parathyroid hormone secreting parathyroid cells. A method within the scope of the present invention can therefore be carried out by local administration of a neurotoxin to a preganglionic sympathetic (i.e. cholinergic) neuron which innervates a parathyroid cell. The cholinergic, preganglionic, sympathetic neuron synapses with adrenergic, post-ganglionic, sympathetic fibers, and these later sympathetic neurons have a stimulatory effect upon parathyroid hormone secretion by parathyroid gland chief cells. Preferably, the sympathetic ganglion to which a neurotoxin is administered, according to the preset invention, is a cervical ganglion.

Cervical ganglion block according to the present invention can be carried out in the same manner as a celiac plexus block. Thus, the neurolytic celiac plexus block is a known procedure for treating intractable pain resulting from upper abdominal viscera cancer. *Reg Anest Pain Med* 1998; 23(1):37–48. Thus, it is known to inject the celiac plexus with ethanol or phenol to provide relief from the pain which can result from pancreatic cancer or from pancreatitis. *AJG* 1999;94(4):872–874. Hence, an antinociceptive injection of the cervical ganglia can be carried out as by either a percutaneous procedure or as an open (intraoperative) injection. The percutaneous (closed) procedure can be carried out using an anterior approach using a very thin needle (22 Gauge). Cervical ganglion block is preferably carried out with computed tomography (CT) (as opposed to fluoroscopic) needle guidance, using a single thin needle.

Furthermore, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, I have discovered that a surprisingly effective and long lasting therapeutic effect can be achieved by local administration of a neurotoxin to a parathyroid or to a sympathetic ganglion which innervates a parathyroid hormone secreting parathyroid cell of a human patient. In its most preferred embodiment, the present invention is practiced by direct injection into a parathyroid gland, or into a sympathetic ganglion which innervates a parathyroid gland, of a therapeutically effective amount of botulinum toxin, such as botulinum toxin type A. It has been reported that at the neuroglandular junction, the chemical denervation effect of a single injection of botulinum toxin, such as botulinum toxin type A, has a duration of action of up to 27 months.

The present invention includes within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for a cell surface receptor present on a parathyroid hormone secreting parathyroid cell.

Botulinum toxins for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

The route of administration and amount of a neurotoxin (such as a botulinum toxin serotype A, B, C, D, E, F or G) administered according to the present invention for treating a parathyroid disorder can vary widely according to various patient variables including size, weight, age, disease severity, responsiveness to therapy, and solubility and diffusion characteristics of the neurotoxin toxin chosen. Furthermore, the extent of the parathyroid or ganglionic tissue influenced is believed to be proportional to the volume of neurotoxin injected, while the quantity of the denervation is, for most dose ranges, believed to be proportional to the concentration of neurotoxin injected.

Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill). For example, to treat a parathyroid disorder, a solution of botulinum toxin type A complex can be endoscopically or intraperitoneally injected directly into the tissues of the parathyroid, thereby substantially avoiding entry of the toxin into the systemic circulation.

EXAMPLES

The following examples provide those of ordinary skill in the art with specific preferred methods within the scope of the present invention for carrying out the present invention and are not intended to limit the scope of what the inventor regards as his invention. In each of the following examples, the specific amount of a botulinum toxin administered depends upon a variety of factors to be weighed and considered within the discretion of the attending physician and in each of the examples insignificant amounts of botulinum toxin enter appear systemically with no significant side effects. Units of botulinum toxin injected per kilogram (U/kg) below are per kg of total patient weight. For example, 3 U/kg for a 70 kg patient calls for an injection of 210 units of the botulinum toxin.

Example 1

Intraoperative Administration of Neurotoxin

Intraoperative, local administration of a neurotoxin to a parathyroid can be carried out as follows. The procedure can be performed under general endotracheal anesthesia. The patient's neck can be extended by inflating a pillow or inserting a thyroid roll beneath the shoulders. A symmetrical, low, collar incision can then be made in the line of a natural skin crease approximately 1 to 2 cm above the clavicle. The incision can be carried through the skin, subcutaneous tissue, and platysma muscle down to the dense cervical fascia that overlies the strap muscles and anterior jugular veins. The upper flap can then be raised to a level cephalad to the cricoid cartilage. Care is taken to avoid cutting sensory nerves. A small lower flap is also elevated to the level of the manubrial notch. Performing dissection of the flaps in the plane between the platysma muscle and the fascia overlying the strap muscles results in minimal bleeding. The cervical fascia is then incised vertically in the midline.

Exposure of the parathyroid glands can generally be achieved by retracting the sternohyoid and sternothyroid muscles laterally Digital or blunt dissection frees the parathyroids from the surrounding fascia. An exposed parathyroid gland can be directly injected with from 0.1 to 50 units of a botulinum toxin, such as botulinum toxin type A. Care should be taken to ensure that the parathyroid glands are not excised or devascularized. Within one to seven days, parathyroid hormone secretion is substantially increased due to removal of cholinergic inhibition and this effect persists for from about 2 to about 6 months.

Example 2

Local Administration of Neurotoxin to a Parathyroid

Local administration of a neurotoxin directly to or to the vicinity of a parathyroid gland can be accomplished by several methods. For example, by parathyroid endoscopy. An endoscope used for parathyroid therapy can be modified to permit its use for direct injection of a neurotoxin, such as a botulinum toxin directly into parathyroid tissue. See for example U.S. Pat. No. 5,674,205. Once appropriately located, a hollow needle tip can be extended from the endoscope into parathyroid tissue and through which needle the neurotoxin can be injected into the parathyroid tissue of one or more of the parathyroid glands.

Additionally, fine needle aspiration for parathyroid biopsy purposes is known and can be used to inject a neurotoxin, rather than to aspirate parathyroid tissue. From 0.1 to 50 units of a botulinum toxin, such as botulinum toxin type A can thereby be injected into one or more of the parathyroid glands. Within one to seven days, parathyroid hormone secretion is substantially increased due to removal of cholinergic inhibition and this effect persists for from 2 to 6 months.

Example 3

Treatment of Hypoparathyroidism with Botulinum Toxin Type A

A 43 year old male is diagnosed with hypoparathyroidism. Between about 0.1 U and about 50 U of a botulinum toxin type A preparation (for example between about 0.1 units and about 50 units of BOTOX®) is injected directly into one or more of the parathyroid glands, using one of the techniques set forth in Examples 1 or 2 above. Within 1–7 days the symptoms of the hypoparathyroidism are alleviated and parathyroid hormone levels return to substantially normal levels. Alleviation of the parathyroid disorder persists for at least about 2 months to about 6 months.

Example 4

Treatment of Hypoparathyroidism with Botulinum Toxin Type B

A 52 year old female is diagnosed with hypoparathyroidism. Between about 20 units and about 1000 units of a botulinum type B preparation is injected directly into one or more of the parathyroids, using one of the techniques set forth in Examples 1 or 2 above. Within 1–7 days the symptoms of the hypoparathyroidism are alleviated. Parathyroid hormone levels return to substantially normal levels. Alleviation of the parathyroid disorder persists for at least about 2 months to about 6 months.

Example 5

Treatment of Hypoparathyroidism with Botulinum Toxin Type C

A 58 year old female is diagnosed with hypoparathyroidism. Between about $10^{-3}$ U/kg and about 35 U/kg of a botulinum toxin type C preparation (for example between about 10 units and about 10,000 units of a botulinum type C preparation) is injected directly into one or more of the parathyroids, using one of the techniques set forth in Examples 1 or 2 above. Within 1–7 days the symptoms of the hypoparathyroidism are alleviated. Parathyroid hormone levels return to substantially normal levels. Alleviation of the parathyroid disorder persists for at least about 2 months to about 6 months.

Example 6

Treatment of Hypoparathyroidism with Botulinum Toxin Type D

A 56 year old obese female is diagnosed with hypoparathyroidism. Between about $10^{-3}$ U/kg and about 35 U/kg of a botulinum toxin type D preparation (for example between about 10 units and about 10,000 units of a botulinum type D preparation) is injected directly into one or more of the parathyroids, using one of the techniques set forth in Examples 1 or 2 above. Within 1–7 days the symptoms of the hypoparathyroidism are alleviated. Parathyroid hormone levels return to substantially normal levels. Alleviation of the parathyroid disorder persists for at least about 2 months to about 6 months.

Example 7

Treatment of Hypoparathyroidism with Botulinum Toxin Type E

A 61 year old female is diagnosed with hypoparathyroidism. Between about $10^{-3}$ U/kg and about 35 U/kg of a botulinum toxin type E preparation (for example between about 10 units and about 10,000 units of a botulinum type E preparation) is injected directly into one or more of the parathyroids, using one of the techniques set forth in Examples 1 or 2 above. Within 1–7 days the symptoms of the hypoparathyroidism are alleviated. Parathyroid hormone levels return to substantially normal levels. Alleviation of the parathyroid disorder persists for at least about 2 months to about 6 months.

Example 8

Treatment of Hypoparathyroidism with Botulinum Toxin Type F

A 52 year old male is diagnosed with hypoparathyroidism. Between about $10^{-3}$ U/kg and about 35 U/kg of a botulinum toxin type F preparation (for example between about 10 units and about 10,000 units of a botulinum type F preparation) is injected directly into one or more of the parathyroids, using one of the techniques set forth in Examples 1 or 2 above. Within 1–7 days the symptoms of the hypoparathyroidism are alleviated. Parathyroid hormone levels return to substantially normal levels. Alleviation of the parathyroid disorder persists for at least about 2 months to about 6 months.

Example 9

Treatment of Hypoparathyroidism with Botulinum Toxin Type G

A 59 year old female is diagnosed with hypoparathyroidism. Between about $10^{-3}$ U/kg and about 35 U/kg of a botulinum toxin type G preparation (for example between about 10 units and about 10,000 units of a botulinum type G preparation) is injected directly into one or more of the parathyroids, using one of the techniques set forth in Examples 1 or 2 above. Within 1–7 days the symptoms of the hypoparathyroidism are alleviated. Parathyroid hormone levels return to substantially normal levels. Alleviation of the parathyroid disorder persists for at least about 2 months to about 6 months.

Example 10

Treatment of Hyperparathyroidism with Botulinum Toxin Type A

A 27 year old female presents with symptoms of progressively worsening myalgias over the last six months. She was otherwise asymptomatic and in good health. Physical examination is unremarkable. Family history and social history are likewise noncontributory. A routine screening serum chemistry profile reveals a serum calcium of 12.0 mg/dl. Serum albumin, protein, magnesium, and chloride are all within normal limits. A parathormone assay level of 211 picograms/ml (normal=10 to 55 picograms/ml) is noted. Two subsequent calcium levels and parathormone levels are persistently elevated and the diagnosis of primary hyperparathyroidism is made. A trial with atropine reduces the parathyroid hormone level.

Between about $10^{-3}$ U/kg and about 35 U/kg of a botulinum toxin type A preparation (for example between about 0.1 units and about 50 units of BOTOX®) is injected directly into the cervical ganglia as follows. A percutaneous procedure is carried out using an anterior approach with the patient in a supine position using a very thin needle (22 Gauge) with computed tomography needle guidance to reach the cervical ganglia. Within 1–7 days the symptoms of the hyperparathyroidism are alleviated. Parathyroid hormone levels return to normal (are lowered). Alleviation of the parathyroid disorder persists for at least about 2 months to about 6 months.

Example 11

Treatment of Hyperparathyroidism with Botulinum Toxin Types B–G

A 62 year old female presents with symptomatic hypercalcemia, serum calcium of 1–1.6 mg/dL above normal values, a creatinine clearance reduction greater than 30%, a 24-hr. urine calcium excretion >400 mg, and a bone mass <2S.D.'s below normal. A diagnosis of primary hyperparathyroidism is made. Between about $10^{31\ 3}$ U/kg and about 35 U/kg of a botulinum toxin type B, $C_1$, D, E, F or G preparation (for example between about 10 units and about 10,000 units of a botulinum type B-G preparation) is injected directly into the cervical ganglia as follows. A percutaneous procedure is carried out using an anterior approach with the patient in a supine position using a very thin needle (22 Gauge) with computed tomography needle guidance to reach the cervical ganglia. Within 1–7 days the symptoms of the hyperparathyroidism are alleviated and parathyroid hormone levels return to substantially normal levels. Alleviation of the hyperparathyroidism persists for at least about 2 months to about 6 months.

Example 12

Treatment of Calcium Metabolism Disorders with Botulinum Toxin Types A-G

A 28 year old female is diagnosed with hypocalcemia. Between about $10^{-3}$ U/kg and about 35 U/kg of a botulinum toxin type A, B, C, D, E, F or G preparation (for example between about 0.1 units and about 50 units of a botulinum toxin type A preparation) is injected directly into one or more of the parathyroids using one of the techniques set forth in Examples 1 or 2 above. Within 1–7 days the symptoms of the hypocalcemia are alleviated. Plasma calcium levels return to substantially normal levels. Alleviation of the hypocalcemia persists for at least about 2 months to about 6 months.

Additionally, to treat hypercalcemia between about $10^{-3}$ U/kg and about 35 U/kg of a botulinum toxin type A, B, C, D, E, F or G preparation (for example between about 0.1 units and about 50 units of a botulinum toxin type A preparation) is injected directly into the cervical ganglia as follows. A percutaneous procedure is carried out using an anterior approach with the patient in a supine position using a very thin needle (22 Gauge) with computed tomography needle guidance to reach the cervical ganglia. Within 1–7 days the symptoms of the hypercalcemia are alleviated. Plasma calcium levels return to normal (are decreased). Alleviation of the hypercalcemia persists for at least about 2 to about 6 months.

Methods according to the invention disclosed herein has many advantages, including the following:

(1) the invention renders unnecessary many surgical procedures for effective treatment of a parathyroid disorder.

(2) systemic drug effects can be avoided by direct local application of a neurotoxin according to the present invention.

(3) the ameliorative effects of the present invention can persists, on average, from about 2 months to about 6 months from a single local administration of a neurotoxin as set forth herein.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local parathyroid administration methods wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type E. Alternately, a combination of any two or more of the botulinum serotypes A–G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

My invention also includes within its scope the use of a neurotoxin, such as a botulinum toxin, in the preparation of a medicament for the treatment of a parathyroid disorder by local administration of the neurotoxin.

Accordingly, the spirit and scope of the following claims should not be limited to the descriptions of the preferred embodiments set forth above.

I claim:

1. A method for treating a primary hyperparathyroid disorder, the method comprising the step of administration of a Clostridial neurotoxin to a sympathetic ganglion which innervates a parathyroid gland of a patient, thereby treating a primary hyperparathyroid disorder.

2. The method of claim 1, wherein the Clostridial neurotoxin is administered in an amount of between $10^{-3}$ U/kg and 35 U/kg.

3. The method of claim 1, wherein the Clostridial neurotoxin is a botulinum toxin.

4. The method of claim 3, wherein the botulinum toxin is selected from the group consisting of botulinum toxin types A, B, $C_1$, D, E, F and G.

5. The method of claim 3, wherein the neurotoxin is botulinum toxin type A.

6. A method for treating a primary hyperparathyroid disorder, the method comprising the step of administration of a therapeutically effective amount of a botulinum toxin to sympathetic ganglion which innervates a parathyroid gland of a patient, thereby treating a primary hyperparathyroid disorder.

7. The method of claim 6, wherein the botulinum toxin is selected from the group consisting of botulinum toxin types A, B, $C_1$, D, E, F and G.

8. A method for treating primary hyperparathyroidism, the method comprising the step of local administration to a sympathetic ganglion which innervates a parathyroid hormone (PTH) secreting parathyroid cell of a therapeutically effective amount of a botulinum toxin, thereby reducing an excessive parathyroid hormone secretion from the parathyroid cell and treating primary hyperparathyroidism.

9. The method of claim 8, wherein the botulinum toxin is selected from the group consisting of botulinum toxin types A, B, $C_1$, D, E, F and G.

10. The method of claim 1, wherein the sympathetic ganglion is a cervical ganglion.

11. The method of claim 6, wherein the sympathetic ganglion is a cervical ganglion.

12. The method of claim 8, wherein the sympathetic ganglion is a cervical ganglion.

* * * * *